Figure 1:
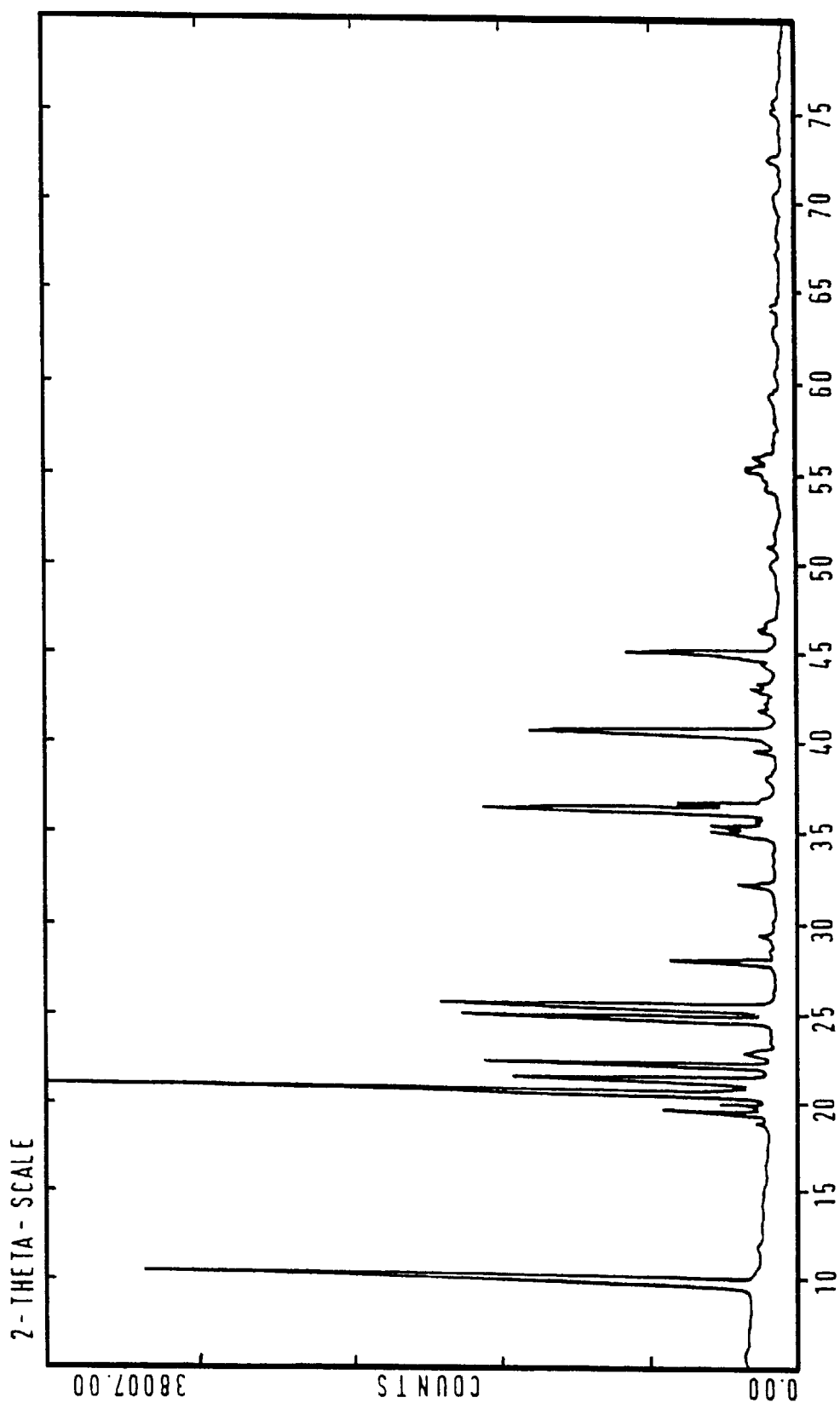

United States Patent [19]
Schwarz et al.

[11] Patent Number: 6,165,511
[45] Date of Patent: Dec. 26, 2000

[54] POLYOL COMPOSITION

[75] Inventors: Eugen Schwarz; Gernot Möschl; Karin Maul, all of Darmstadt, Germany

[73] Assignee: Merck Patent Gesellschaft mit beschrankter Haftung, Germany

[21] Appl. No.: 09/171,536

[22] PCT Filed: Apr. 10, 1997

[86] PCT No.: PCT/EP97/01787

§ 371 Date: Oct. 21, 1998

§ 102(e) Date: Oct. 21, 1998

[87] PCT Pub. No.: WO97/39739

PCT Pub. Date: Oct. 30, 1997

[30] Foreign Application Priority Data

Apr. 22, 1996 [DE] Germany .................... 196 15 418

[51] Int. Cl.⁷ .................................................. A61K 9/14

[52] U.S. Cl. .................... 424/489; 424/488; 424/493; 424/499; 424/479; 424/464; 424/440; 424/441

[58] Field of Search ................................. 424/489, 464, 424/465, 490, 491, 497

[56] References Cited

U.S. PATENT DOCUMENTS 5,876,754  3/1999  Wunderlich et al. ................. 424/489

*Primary Examiner*—Thurman K. Page
*Assistant Examiner*—William E. Benston, Jr.
*Attorney, Agent, or Firm*—Millen, White, Zelano & Branigan, P.C.

[57] ABSTRACT

A polyol composition useful for the production of tablets for consumption. The polyol is obtained by co-spray drying or co-fluidized bed granulating at least two polyols, one of which is a non-hygroscopic polyol, and the non-hygroscopic polyol is present in an amount of at least 80% by weight. An optional binder may be present. An active medicament may be present.

11 Claims, 9 Drawing Sheets

POLYOL COMPOSITION

This Application is a 371 of PCT/EP97/01787 filed Apr. 10, 1997.

The invention relates to a composition obtainable by co-spray-drying or co-fluidized-bed granulation essentially consisting of at least two polyols and, if appropriate, a binder, having a content of at least one non-hygroscopic polyol of more than 80% by weight, and to its use as a tableting aid.

Polyols and polyol mixtures are used to a great extent as noncariogenic additives and carriers, inter alia for pharmaceutical active compounds, tablets to be chewed and sucked, and other products of the pharmaceutical and confectionery industries. Polyols are generally produced by hydrogenation of their underlying sugars. In solid form, they can be obtained both by crystallization and by spray-drying.

The particular advantage of some polyols is that they are also suitable for direct pressing without further aids and additives.

Non-hygroscopic polyols are those polyols which, at a relative humidity of 80%, absorb less than 5% water at room temperature in the course of 7 days.

The known polyols, mannitol, lactitol, isomaltitol, xylitol, have low hygroscopicity of this type, but exhibit poor tableting behaviour (low tablet hardness, crusting, high abrasion). Achieving high tablet hardnesses is fundamentally advantageous, since carriers are frequently used only in small amounts in pharmaceutical formulations and active compounds can drastically decrease the tablet hardnesses, so that a desired formulation cannot be tableted.

Whereas lactitol, isomaltitol and xylitol are rarely used in the production of compressed articles, mannitol is widely used in pharmaceutical formulations.

However, the use of mannitol represents an increase in the amount of work, since it must generally be granulated wet prior to compression with the remaining formula constituents. Directly tabletable mannitol is also commercially available, but, in comparison with sorbitol, it can achieve only unsatisfactory tablet hardnesses.

Using sorbitol, in particular in the case of spray-drying, very good tablet hardnesses are achieved with correspondingly smooth surface of the compressed articles. However, the hygroscopicity of sorbitol is considerably higher than that of the other polyols, which restricts its applicability.

DE 32 45 170 proposes preparing a polyol combination of sorbitol and 10–15% by weight of mannitol by spray-drying. This is intended to increase the flexural strength of the tablets. However, the hygroscopicity remains essentially unchanged. There is no indication there that polyol combinations which were prepared by spray-drying and have mannitol as principle component can achieve improved properties, in particular high binding capacity for active compounds at lower hygroscopicity.

EP 0 528 604 describes a sorbitol and xylitol composition obtainable by co-melting. However, this leads to tablets having a comparatively low hardness.

The object was therefore to provide a polyol composition which can be prepared without problems and whose tableting properties, in particular with regard to tablet hardness and binding capacity, are improved in comparison with known polyols.

It has now been found that a polyol composition obtainable by co-spray-drying comprising at least 80% by weight of one or more non-hygroscopic polyols, on tableting at the same compression pressure, on the one hand gives higher tablet hardnesses and a much smoother surface, and on the other hand has a markedly lower hygroscopicity in comparison with sorbitol.

The invention thus relates to a composition essentially consisting of at least two polyols obtainable by co-spray-drying, which composition comprises at least 80% by weight of at least one non-hygroscopic polyol, in particular mannitol.

The term polyol means sugar alcohols of the general formula

$$CH_2OH—(CHOH)_n—CH_2OH,$$

where n is 2 to 6, preferably 3 to 4,
and their dimeric anhydrides, in particular $C_{12}H_{24}O_{11}$.

In particular, the term polyols means hexitols, such as sorbitol and mannitol, pentitols, such as xylitol, however, other possibilities are also $C_4$ polyalcohols, such as erythritol, or $C_{12}$ polyalcohols, such as lactitol. The term polyol composition means a composition of a plurality of polyols which differ markedly in their composition from compositions arising in the industrial production of mannitol, preferably those compositions which comprise at least two polyols having a different number of carbon atoms, in particular the term means a composition comprising mannitol and at least one other hexitol, in particular sorbitol or a dodecaitol, in particular lactitol.

Preferred embodiments are a) a composition obtainable by dissolving at least two polyols in water and spraying the resulting aqueous mixture in an air stream at a temperature from 120 to 300° C.

b) a composition obtainable by dissolving at least two polyols in water and vortexing the resulting mixture in an air stream at a temperature between 40° and 110° C.

c) a composition where mannitol and sorbitol, mannitol and lactitol or mannitol, sorbitol and lactitol and other polyols, in particular mannitol, sorbitol and lactitol, are used as polyols.

d) a composition where the ratio of mannitol to sorbitol/lactitol is in a range between 80:20 and 99:1, in particular between 90:10 and 98:2. In a particularly preferred embodiment, the ratio is about 95:5, in particular the ratio mannitol:sorbitol:lactitol is in a range from 90:1:9 or 90:9:1 to 98:1:1.

e) a composition according to one of the preceding claims, characterized in that [sic] the water content is less than 1% by weight.

f) a composition which comprises from 0.05 to 5% by weight of a binder.

g) a composition which has filaments, preferably needle-shaped filaments, whose length/width ratio is between 15 and 5 to 1, in a crystal structure.

The invention further relates to compressed articles comprising a composition according to the invention.

The invention further relates to a process for preparing a composition essentially consisting of at least two polyols and, if appropriate, a binder, comprising the following steps:

a) preparing an aqueous solution of at least two polyols, the solution comprising more than 80% of one or more non-hygroscopic polyols, based on the total polyol content, b1) spraying the resulting solution in an air stream at a temperature between 120 and 300° C., the water being evaporated, or b2) vortexing the resulting solution in an air stream at a temperature between 40 and 110° C., the water being evaporated.

In a particularly preferred embodiment, the polyol composition according to the invention essentially consists of 85 to 99% by weight, in particular 88 to 98% by weight, of mannitol and 5 to 15% by weight, in particular 6 to 12% by weight, on one or two polyols selected from lactitol and sorbitol.

Preferably, the polyol composition according to the invention comprises more than 90% by weight, and less than 99% by weight, of mannitol.

For the spray-drying, an aqueous solution of at least two polyols is used. The solids content is set in advance to about 30 to about 75% by weight, in particular 50 to 72% by weight, preferably by mixing, at a temperature of 80° C., two or more polyol solutions in the desired ratio. The spraying is performed by atomizing using nozzles, preferably using a centrifugal atomizer, into a dry, centrifugally injected air stream heated to a temperature of 120–300° C., preferably 140–190° C. The amount of the polyol solution supplied is matched to that of the injected hot air in such a manner that the polyol is dried to a water content of about 0.3 to about 1% by weight. In any case, the water content should be below 1% by weight.

The fluidized-bed granulation is carried out as described, for example, in P. Grassmann, F. Widmer "Einführung in die thermische Verfahrenstechnik" [Introduction to Thermal Process Engineering], Verlag DeGruyter, Berlin 1974.

The polyol agglomerates which are obtained here by dehydrating the polyol solution droplets are heated in the spray-drying to a temperature of about 50 to about 70° C., while the injected air is cooled to about the same temperature. The polyol composition is collected in vessels and is, after cooling, directly suitable for producing tablets, compressed articles or chewing gum.

The polyols thus obtained, on account of their filamentous microstructure, have a binding capacity for active compounds which is far higher than that of crystalline mannitol and which corresponds to that of pure sorbitol, but without exhibiting its disadvantageous hygroscopicity.

The polyol composition thus characterized has a number of advantageous tableting properties:

Surprisingly, it can be observed that using the polyol composition according to the invention, at the same compression force, harder tablets having a markedly smoother surface can be produced than using the known mannitol quality grades, including the known TLC mannitol types and mechanical polyol triturations. The tablet hardness essentially determines the sucking properties. Using a polyol composition according to the invention, optimally smooth, hard tablets can be produced even at very low compression forces. Tableting machines by means of which the polyol composition according to the invention is compressed can therefore operate at relatively low compression forces and are subject in this manner to lower wear.

Owing to the filamentous structure, the polyol composition according to the invention is able to bind even relatively large amounts of additives, such as pharmaceutical active compounds, dyes or other admixtures. Even at a high loading with additives, homogeneous mixtures are obtained, and the compressed articles produced therefrom have a uniform appearance.

On account of the special type of production by spraying an aqueous solution, it is possible to distribute water-insoluble and water-soluble admixtures, such as citric acid, sweeteners, in particular acesulfame-K, Aspartam®, saccharin, cyclamate and sucralose, neohesperidin DC, dyes and pharmaceutical active compounds, preferably vitamins, in particular ascorbic acid and the like, homogeneously in the polyol composition or the tablets produced therefrom.

The binders to be added if appropriate are familiar to those skilled in the art and serve to increase the strength of the composition. Binders which are preferred are cellulose derivatives, in particular hydroxypropylemethylcellulose, carboxymethylcellulose or starch.

In addition to the polyol composition according to the invention, the compressed articles according to the invention comprise one or more constituents selected from the group consisting of: pharmaceutical active compounds and substances permitted by food legislation. Preferred substances permitted by food legislation are natural, nature-identical or synthetic aromas or flavourings, vitamins, trace elements, minerals, dyes, lubricants, release agents, sweeteners, stabilizers or antioxidants. The content of these constituents is preferably between 0.01 and 80%, in particular between 0.1 and 30%.

These compressed articles are produced in a manner known per se by mixing the constituents in dry form and then tableting them.

PREPARATION EXAMPLES

Example 1

A 50% aqueous solution which comprises, based on the dry mass, 95 parts of mannitol, 1.5 parts of hydroxyproplymethylcellulose and 3.5 parts of sorbitol is prepared.

This polyol solution is sprayed by means of a centrifugal atomizer at about 50° C. into the upper part of a cylindrical stainless steel tower. At the same time, air heated to about 160° C. and polyol granules are injected tangentially into the spraying zone. The solids stream is taken off via a cooling drum and then divided: One part is returned to the spraying zone of the tower and the remainder is screened, dried further on a fluidized bed and then packaged. The resulting product can be compressed without problems and leads to tablets having a very smooth surface.

Example 2

A 50% aqueous solution which, based on the dry mass, comprises 90.5 parts of mannitol and 9.5 parts of sorbitol, is prepared. The product obtained by spray-drying in a similar manner to Example 1 can be compressed without problems, results similar to those described in Example 1 being achieved.

Example 3

A 50% aqueous solution which comprises, based on the dry mass, 95 parts of mannitol and 5 parts of sorbitol, is prepared. The product obtained by spray-drying in a similar manner to Example 1 may be compressed without problems, results similar to those described in Example 1 being achieved.

Example 4

A 50% aqueous solution which comprises, based on the dry mass, 95 parts of mannitol and 5 parts of lactitol, is prepared. The product obtained by spray-drying in a similar manner to Example 1 may be compressed without problems, results similar to those described in Example 1 being achieved.

Scanning electron micrographs recorded using a Jeol 630 F scanning electron microscope at 50x and 5000x enlargement of the polyol compositions according to Examples 2 and 4, of commerically available TLC mannitol, of a mechanical trituration of 90.5% mannitol and 9.5% sorbitol and of a mechanical trituration of 90% mannitol and 10% lactitol were assesed.

The micrographs of the Example 2 and 4 compositions clearly show that the preparations according to the invention are agglomerates of extremely fine needle-shaped crystallites, whereas, in contrast, the agglomerates of TLC mannitol consist, in a significantly differentiable manner, of relatively large crystallites.

The micrographs of the mechanical mixtures show both agglomerate types.

Example 5

Tablets for sucking

| | |
|---|---|
| Polyol composition prepared in accordance with Example 2 with addition of 0.8% by weight of citric acid, based on polyol used. Dry aroma of fruits (various flavour notes) | 491.0 parts by weight |
| | 1.5 parts by weight |
| Magnesium stearate | 2.5 partS by weight |

The constituents are mixed and compressed at a compression pressure of 30 kN to give tablets of 13 mm diameter and 500 mg weight.

Example 6

Vitamin C tablets

| | |
|---|---|
| Ascorbic acid | 105.0 parts by weight |
| Orange aroma | 10.0 parts by weight |
| Polyol composition prepared in accordance with Example 2 | 1377.5 parts by weight |
| Magnesium stearate | 7.5 parts by weight |

The constituents are mixed and compressed at a compression pressure of 11 kN to give tablets of 18 mm diameter and 1500 mg weight.

Example 7

Caffeine tablets

| | |
|---|---|
| Polyol composition according to Example 1 | 462.5 parts by weight |
| Coffee aroma | 25.0 parts by weight |
| Caffeine | 10.0 parts by weight |
| Magnesium stearate | 2.5 parts by weight |

The constituents are mixed and compressed at a compression pressure of 30 kN to give tablets of 13 mm diameter and 500 mg weight.

Example 8

Study of tableting properties

Tablets are prepared using various polyols:

| | | | |
|---|---|---|---|
| Tablet diameter: | 11 mm | Tablet weight: | 450 mg |
| Tablet height: | 3.7 to 3.9 mm | Compression pressure: | 15 kN |

Polyol used
  A: Spray-dried mannitol:sorbitol=90.5:9.5 from Example 2
  B: Spray-dried mannitol:sorbitol=95:5 from Example 3
  C: Spray-dried mannitol:lactitol=95:5 from Example 4
  D: Commercially conventional TLC mannitol
  E: Crystallized mannitol
  F: Mechanical trituration of mannitol with sorbitol in a ratio of 95:5
  G: Mechanical trituration of mannitol with lactitol in a ratio of 95:5
  H: Sorbitol, Instant Pharma, obtainable from Merck KGaA, Darmstadt.

The tableting properties of these products can be taken from Table I.

TABLE I

| Polyol | A | B | C | D | E | F | G | H |
|---|---|---|---|---|---|---|---|---|
| Tablet hardness (kN) | 281 | 229 | 195 | 85 | 72 | 85 | 80 | 215 |
| Abrasion (%) | 0.14 | 0.2 | 0.16 | 0.3 | 5.9 | 1.2 | 2.0 | 0.18 |

The tablets according to the invention, on account of their hardness and their low abrasion, have more pleasant sucking properties than the comparison samples (mannitol).

Example 9

Study of the hygroscopicity of the polyols

The polyols B, C, D, E, F, H from Example 8 are stored for 7 days at an atmospheric humidity of 76%.

The water absorption of the products can be taken from Table II

TABLE II

| Polyol | B | C | D | E | F | H |
|---|---|---|---|---|---|---|
| Water absorption (%) | 1.8 | 0.44 | 0.4 | 0.05 | 1.9 | 5.3 |

The polyol mixtures prepared according to the invention show, in comparison with commercially available TLC mannitol (D), a slightly higher hygroscopicity, but this is markedly reduced in comparison with sorbitol (H).

Example 10

Study of the loading capacity (ordered stable mixtures) of the polyols.

Polyols B and D are sieved through a sieve having a pore size of 200 $\mu$m and mixed with 3% by weight of a pharmaceutical active compound having a particle size of less than 40 $\mu$m.

The mixture thus obtained is briefly subjected to air discharge over an air-jet sieve of 100 $\mu$m. The active compound remaining in the mixture is determined colorimetrically.

The loading capacity of the carrier material thus determined (recovery rate in %) can be taken from Table III.

| Polyol | B | D | H |
|---|---|---|---|
| Capacity (at 3%) | 83 | 72 | 83 |

The loading capacity is markedly improved in comparison with TLC mannitol.

Example 11

Comparison between the tabletting behaviour of polyol compositions and commercially available TLC-mannitol The test material corresponds to the composition prepared according to Example 3 (95 parts of mannitol, 5 parts of sorbitol), which is mixed with 1% of magnesium stearate based on the total weight and pressed to form tablets. In comparison, the same weight ratios are triturated together. In addition, corresponding compositions are studied which were prepared by co-spray-drying of 60 parts of mannitol with 40 parts of sorbitol or by triturating together corresponding weight ratios of mannitol and sorbitol and were then mixed with 1% of magnesium stearate, based on the total mass.

| | |
|---|---|
| Tabletting press | Korsch EK 0 |
| Tablet diameter | 11 mm |
| Pressing tools | flat, faceted with breaking notch |
| Tablet weight | 500 mg |
| Fracture strength tester | Erweka TBH 28 (converted to Schleuniger) |
| Abrasion test | Erweka Friabilator TA |

The tablets prepared were subjected to an X-ray structural analysis and a DSC analysis.

The X-ray diffraction analysis was performed with a Siemens D5000 powder diffractometer.
Sample preparation:

Approximately 0.5 g of the sample is lightly ground in an agate mortar, applied to a Mylar film and covered with a second Mylar film. The Mylar film was fixed to a sample holder suitable for the diffractometer.
Measurement conditions:

Transmission mode, generator power 40 kV/30 mA, Cu-K$\alpha$1-radiation (primary monochromator), positionally sensitive detector (3.3 kV), measuring range: 5°–80° (2$\theta$); step time: 24 s; step size; 0.05°.
Procedure:

The measurement is begun immediately after sampling. The X-ray diffractogram recorded is compared with the reference diffractograms.

DSC analysis (Differential Scanning Calorimetry) was performed using a cell (System 2100) with a central computer, module interface, DSC cellbase and DSC cell from TA Instruments (previously Du Pont).

| Measurement conditions | |
|---|---|
| Sample vessel | standard open cup |
| Atmosphere | 0.15 1/min $N_2$ |
| Temperature calibration | o-terphenyl (T = 55.1° C.) |
| | anisic acid (T = 183.2° C.) |
| Heating rate | 2° C./min |
| Sample vessel starting temperature | room temperature |

The DSC measurement is performed from room temperature up to 180° C.

The DSC curve is evaluated between 50 and 175° C. using the programme "General 4.1" and the heating rate is reported in °C./min.

Figure 2:
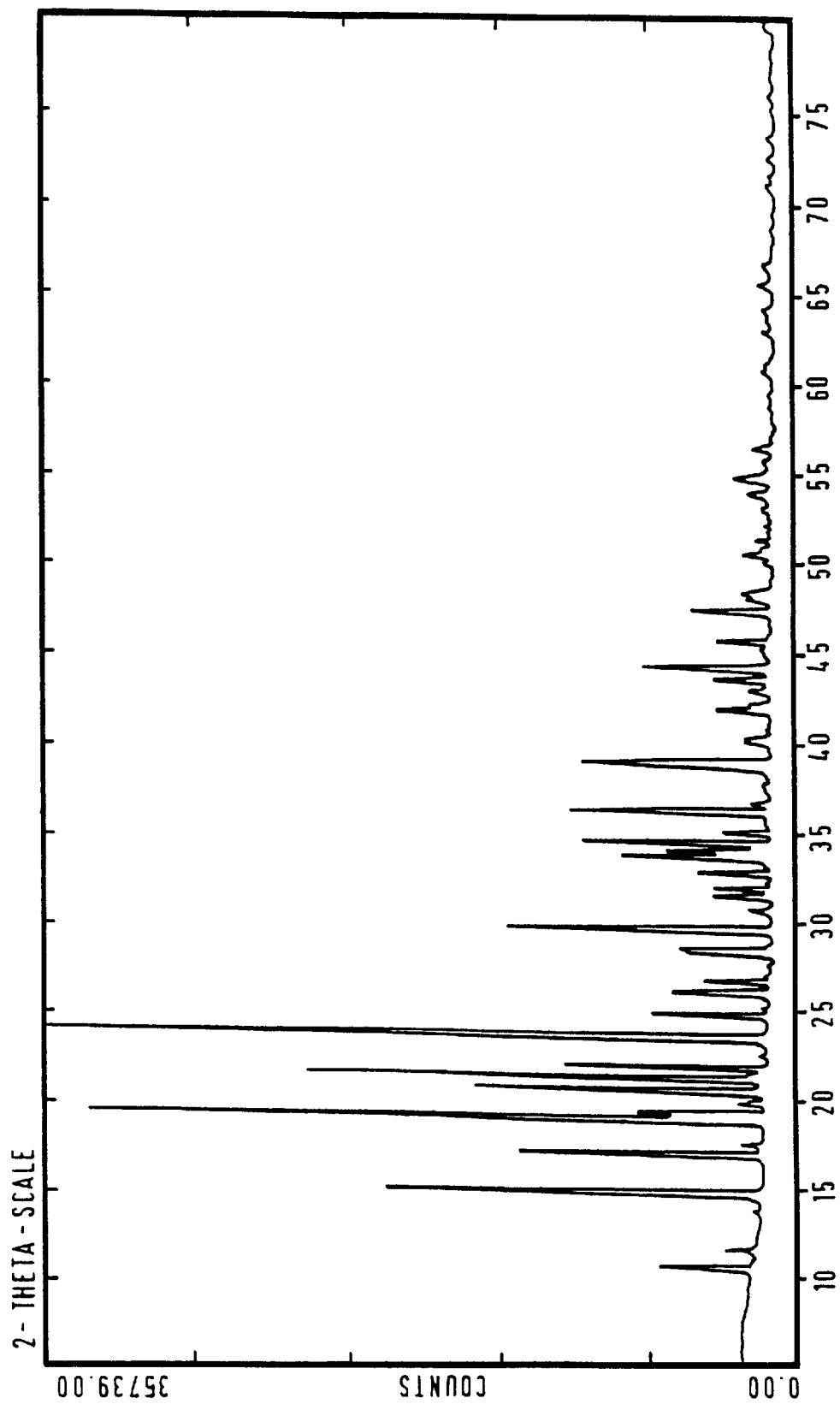
Figure 3:
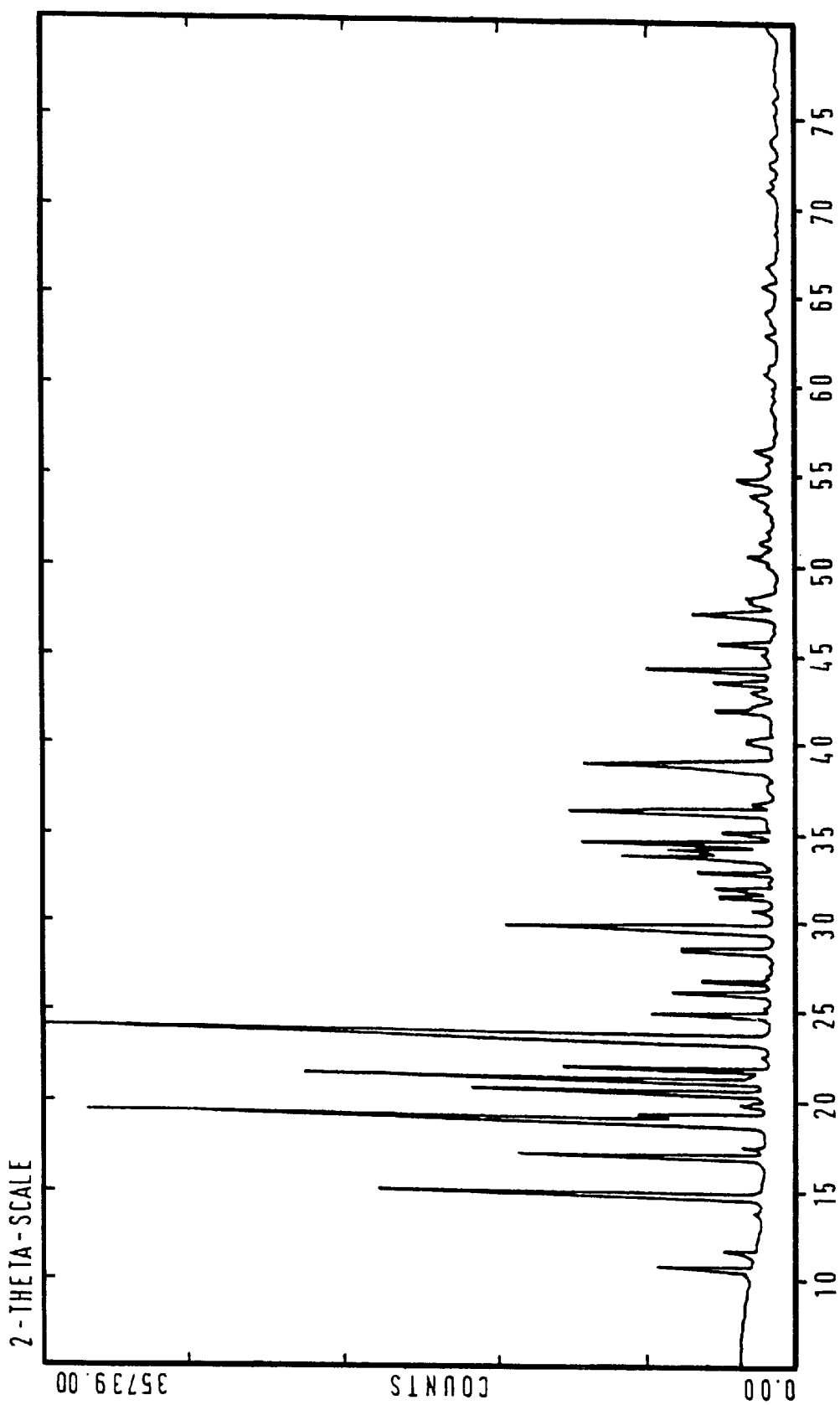
Figure 4:
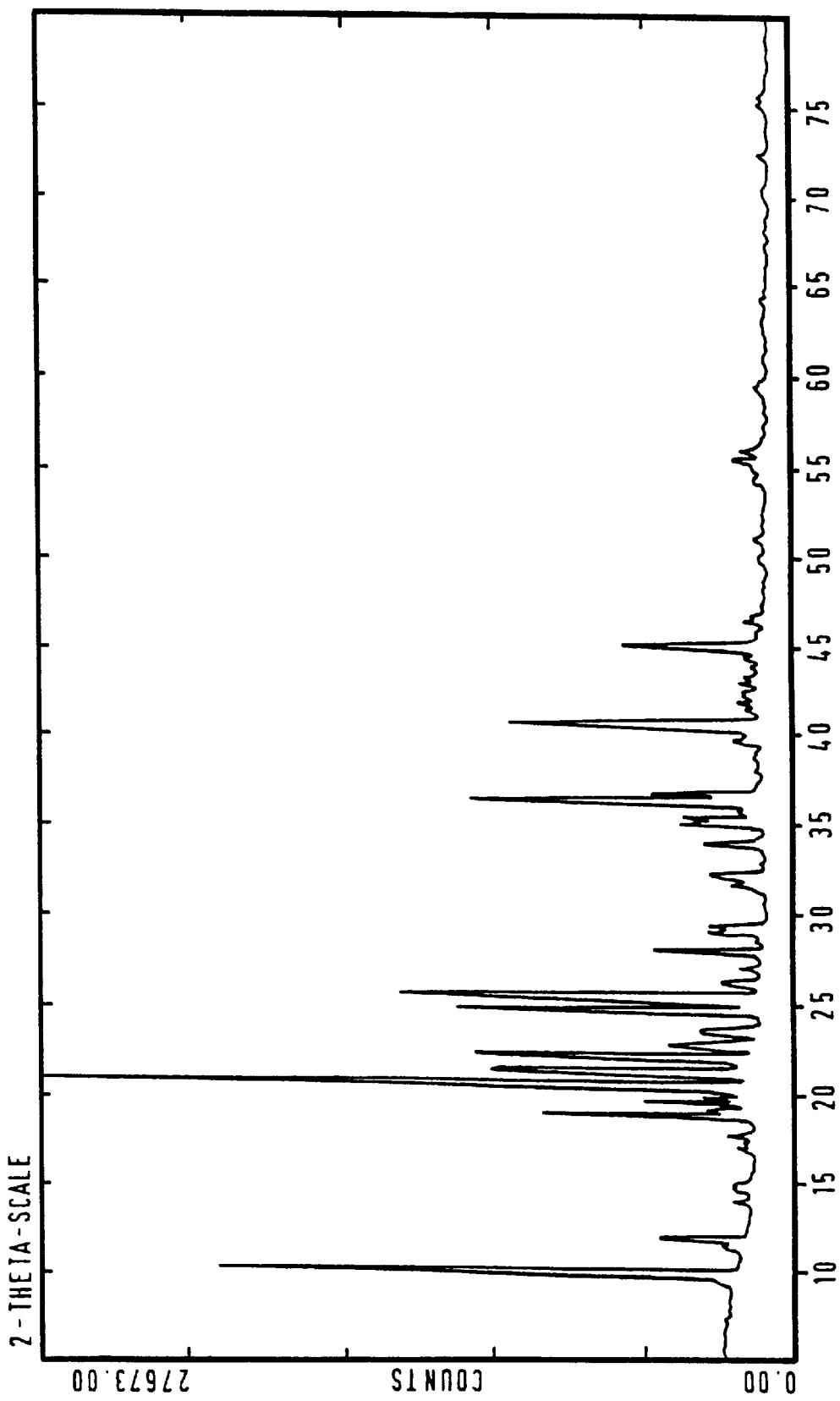
Figure 5:
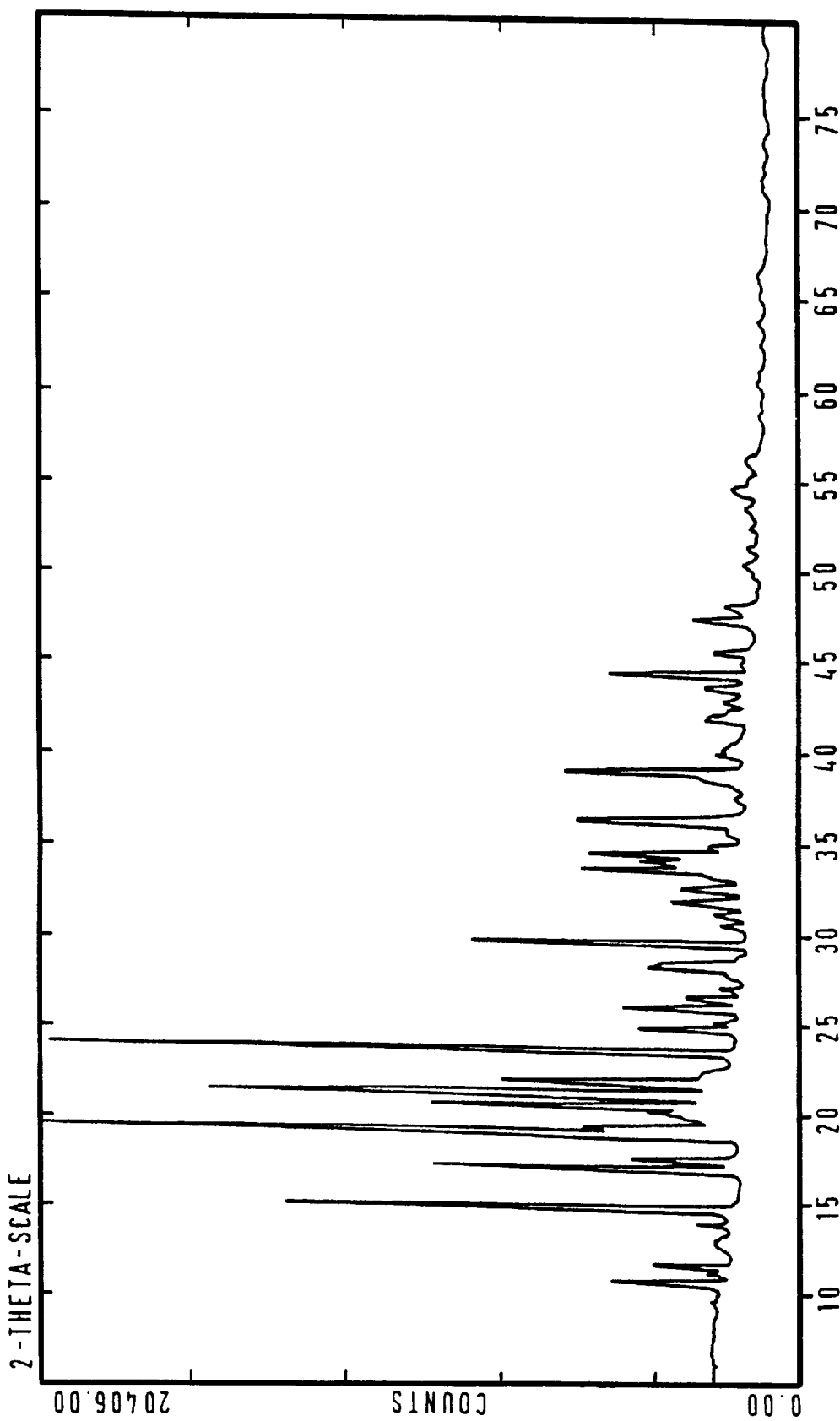
Figure 6:
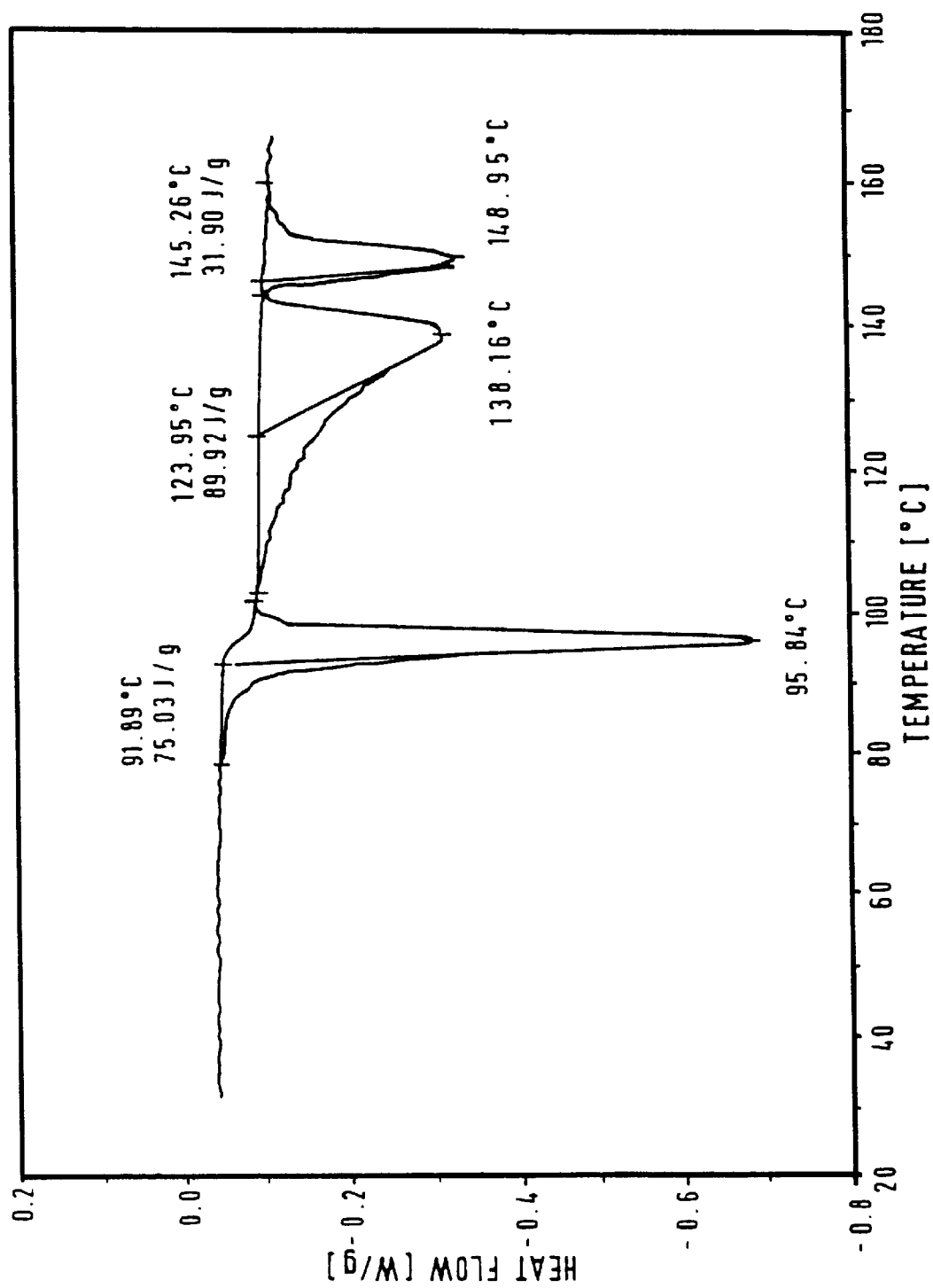
Figure 7:
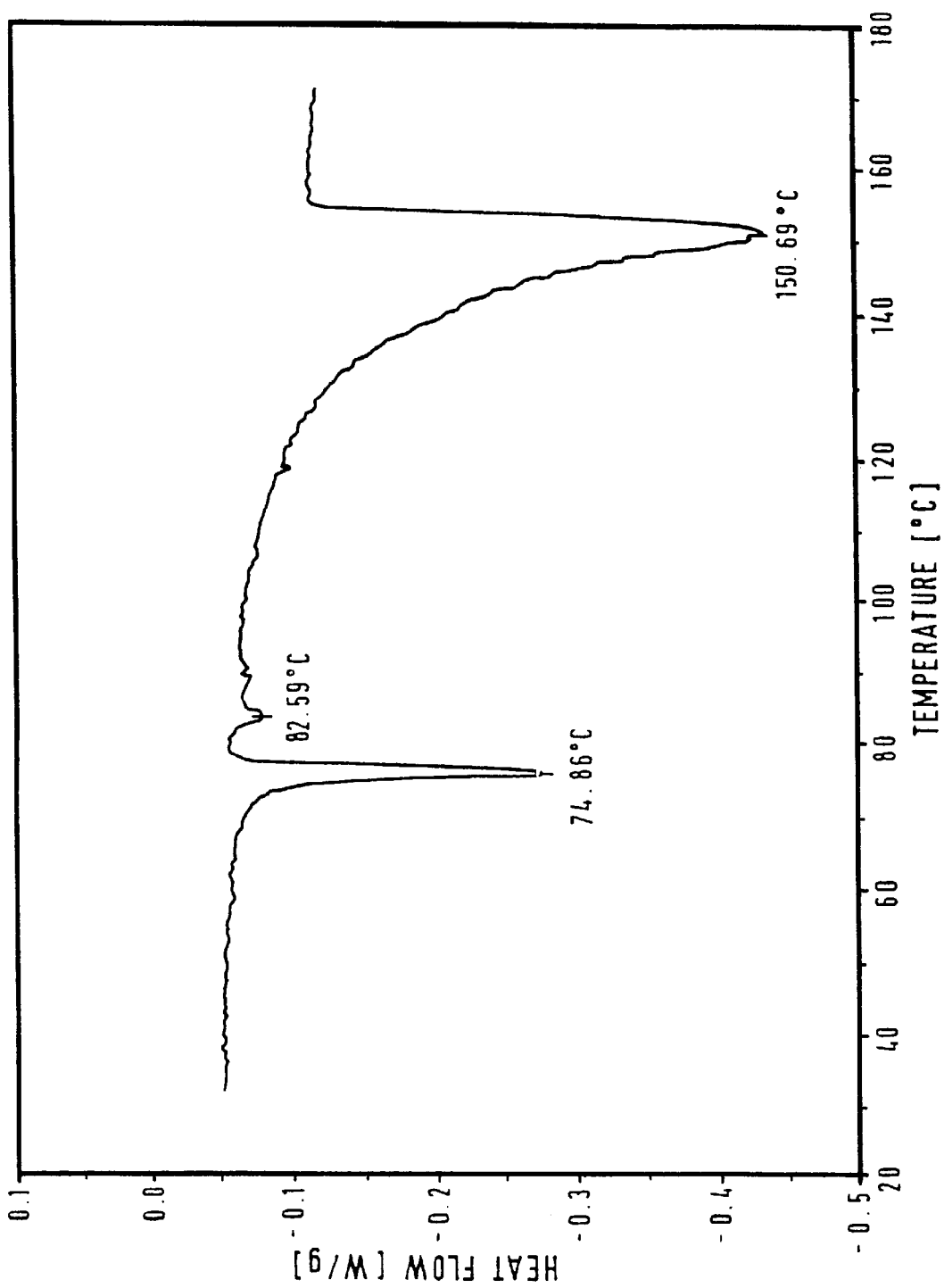
Figure 8:
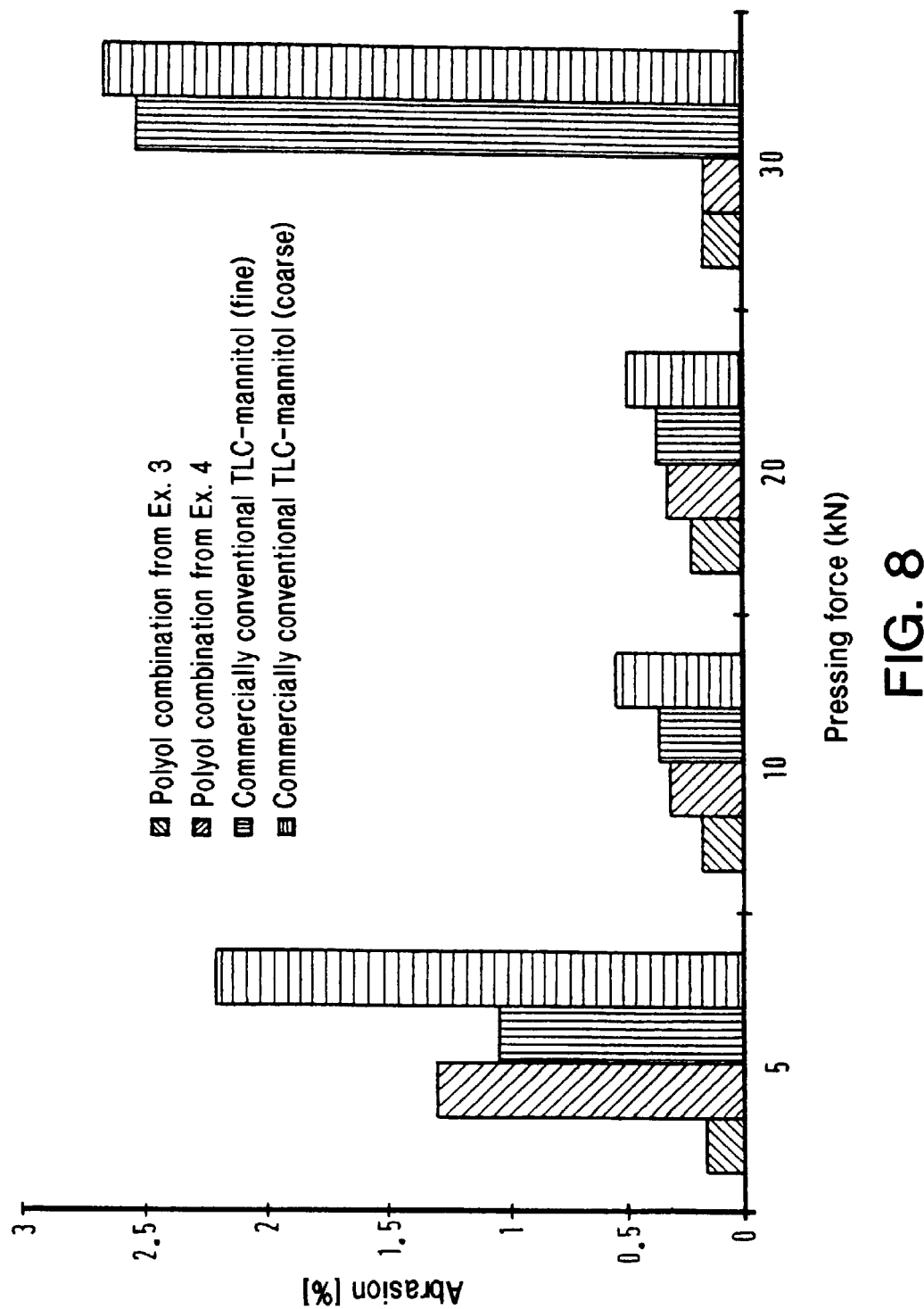
Figure 9:
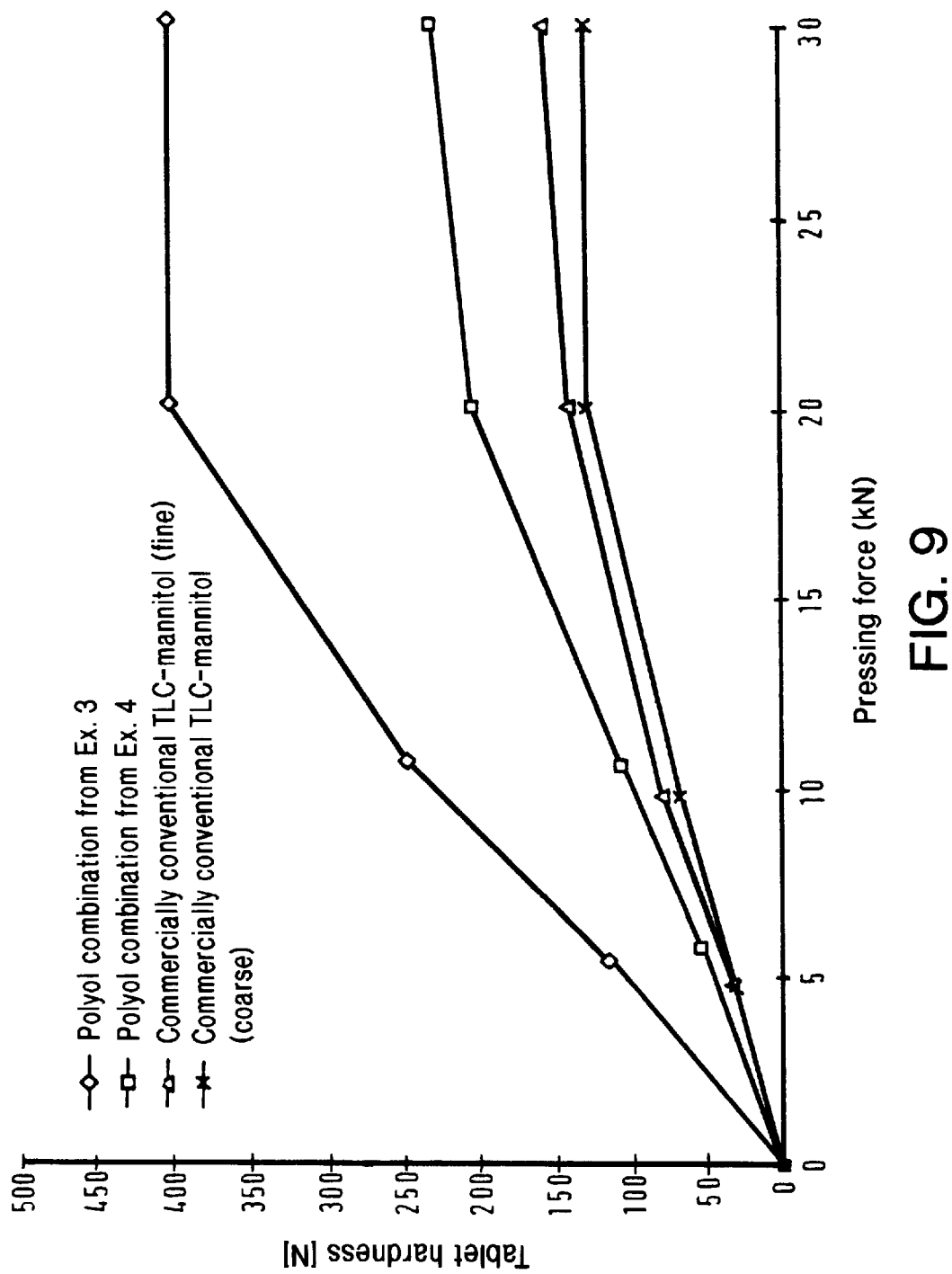

FIGS. 1–9 each relate to the following:

FIG. 1

Mannitol:sorbitol 95:5, triturated

X-ray structural analysis: CT: 24.0 s, SS: 0.050 dg, WL: 1.5406

FIG. 2

Mannitol:sorbitol 95:5, co-sprayed

X-ray structural analysis: CT: 24.0 s, SS: 0.050 dg, WL: 1.5406 A

FIG.: 3

Mannitol:sorbitol 95:5, co-sprayed

X-ray structural analysis: CT: 24.0 s, SS: 0.050 dg, WL: 1.5406 A

FIG.: 4

Mannitol:sorbitol 60:40, triturated

X-ray structural analysis: CT: 24.0 s, SS: 0.050 dg, WL: 1.5406 A

FIG.: 5

Mannitol:sorbitol 60:40, co-sprayed

X-ray structural analysis: CT: 24.0 s, SS: 0.050 dg, WL: 1.5406 A

FIG.: 6

Mannitol:sorbitol 60:40, triturated DSC analysis

FIG.: 7

Mannitol:sorbitol 60:40, co-sprayed DSC analysis

FIG.: 8

Comparison between the tabletting behaviour of polyol combinations and commercially available TLC-mannitol abrasion

FIG.: 9

Comparison between the tabletting behaviour of polyol combinations and commercially available TLC-mannitol: Tablet Hardness

What is claimed is:

1. A process for the preparation of a composition consisting essentially of at least two polyols comprising the following steps:

a) preparing an aqueous solution of at least two polyols, the solution comprising more than 80% of one or more non-hygroscopic polyols based on the total polyol content, and b) spraying the resulting solution in an air stream at a temperature between 120 and 300 C., the water being evaporated, whereby the composition thus prepared contains a filamentous microstructure.

2. A process as claimed in claim 1, further comprising including a binder.

3. A process as claimed in claim 1, wherein the non-hygroscopic polyol is selected from the group consisting of mannitol, sorbitol, lactitol, isomaltitol, xylitol and erythritol.

4. A process as claimed in claim 1, wherein the polyols are mannitol and sorbitol, mannitol and lactitol, or mannitol, sorbitol, and lactitol.

5. A process as claimed in claim 4, wherein, the ratio of mannitol to sorbitol/lactitol is in a range between 80:20 and 99:1.

6. A process as claimed in claim 4, wherein the ratio of mannitol:sorbitol; lactitol is in a range between 90:1:9 or 90:9:1 and 98:1:1.

7. A process as claimed in claim 1, wherein the water content of the resulting composition is less than 1% by weight.

8. A process as claimed in claim 2, wherein the binder is present in an amount of from 0.05 to 5% by weight of binder.

9. A process as claimed in claim 4, wherein the polyols are mannitol, sorbitol, and lactitol.

10. A process as claimed in claim 9, further containing polyols other than mannitol, sorbitol, and lactitol.

11. A process as claimed in claim 4, wherein the ratio of mannitol to sorbitol/lactitol is in a range between 90:10 and 98:2.

* * * * *